US010167358B2

(12) United States Patent
Richter

(10) Patent No.: US 10,167,358 B2
(45) Date of Patent: Jan. 1, 2019

(54) PROCESS FOR MODIFYING ISOCYANATES WITH USE OF CYCLIC AMMONIUM SALTS AS CATALYST

(71) Applicant: Covestro Deutschland AG, Leverkusen (DE)

(72) Inventor: Frank Richter, Leverkusen (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 15/753,004

(22) PCT Filed: Aug. 15, 2016

(86) PCT No.: PCT/EP2016/069353
§ 371 (c)(1),
(2) Date: Feb. 15, 2018

(87) PCT Pub. No.: WO2017/029266
PCT Pub. Date: Feb. 23, 2017

(65) Prior Publication Data
US 2018/0244826 A1    Aug. 30, 2018

(30) Foreign Application Priority Data
Aug. 17, 2015 (EP) .................... 15181246

(51) Int. Cl.
| C08G 18/12 | (2006.01) |
| B01J 31/02 | (2006.01) |
| C07D 295/037 | (2006.01) |
| C08G 18/02 | (2006.01) |
| C08G 18/20 | (2006.01) |
| C08G 18/16 | (2006.01) |
| C07C 53/10 | (2006.01) |
| C07C 53/128 | (2006.01) |

(52) U.S. Cl.
CPC ........ C08G 18/022 (2013.01); B01J 31/0239 (2013.01); B01J 31/0282 (2013.01); C07D 295/037 (2013.01); C08G 18/2018 (2013.01)

(58) Field of Classification Search
CPC .................................................. C08G 18/12
USPC ......................................................... 528/52
See application file for complete search history.

(56) References Cited

U.S. PATENT DOCUMENTS

| 4,865,795 A | 9/1989 | Shiomura et al. |
| 4,937,339 A | 6/1990 | Shiomura et al. |
| 4,960,848 A | 10/1990 | Scholl et al. |
| 5,013,838 A | 5/1991 | Scholl |
| 5,914,383 A | 6/1999 | Richter |
| 6,090,939 A | 7/2000 | Richter et al. |
| 6,107,484 A | 8/2000 | Richter et al. |
| 8,754,184 B2 | 6/2014 | Doyle et al. |
| 9,458,097 B2 | 10/2016 | Richter et al. |

FOREIGN PATENT DOCUMENTS

| CA | 2244486 | 2/1999 |
| EP | 0235388 A2 | 9/1987 |
| EP | 0379914 A2 | 8/1990 |
| EP | 0447074 B1 | 12/1995 |
| EP | 0962455 A1 | 12/1999 |
| WO | 2011060407 A1 | 5/2011 |

OTHER PUBLICATIONS

Laas et al., The Synthesis of Aliphatic Polyisocyanates Containing Biuret, Isocyanurate or Uretdione Backbones for use in Coating, J. prakt. Chem. 336, (1994) pp. 185-200.
Houben-Weyl, Methoden der Organischen Chemie, 4th Edition, vol. XI/2, pp. 591-640.
Wendisch et al., Kernresonanzspektroskopische Bieträge zur Struktur und Stereochemie von (cyclo)aliphatischen Isocyanaten und deren Folgeprodukten, Die Angewandte Makromolekulare Chemie 141, 1986, pp. 173-183.

Primary Examiner — Duc Truong
(74) Attorney, Agent, or Firm — John E. Mrozinski, Jr.

(57) ABSTRACT

The invention relates to a process for modifying isocyanates where at least one organic isocyanate with NCO functionality >1 is oligomerized in the presence of at least one catalyst, characterized in that the catalyst comprises, as isocyanatemodification catalysts, at least one cyclic ammonium salt having a cation of the formula (I) (formula I), where the N-containing substituents $R^1$ and $R^2$ are mutually independently identical or different aliphatic, cycloaliphatic, aromatic or araliphatic $C_1$ to $C_{20}$ moieties which are saturated or unsaturated, linear or branched, optionally substituted and/or interrupted by heteroatoms from the group of oxygen, sulphur and nitrogen, and Y is a substituted or unsubstituted, linear or branched $C_2$ to $C_{20}$ segment optionally interrupted by heteroatoms from the group of oxygen, sulphur and nitrogen or else intempted by aromatic rings, and optionally containing other rings. The invention further relates to the use of such a catalyst.

18 Claims, No Drawings

PROCESS FOR MODIFYING ISOCYANATES WITH USE OF CYCLIC AMMONIUM SALTS AS CATALYST

CROSS REFERENCE TO RELATED APPLICATIONS

This application is a national stage application under 35 U.S.C. § 371 of PCT/EP2016/069353, filed Aug. 15, 2016, which claims priority to European Application No. 15181246.8, filed Aug. 17, 2015, both of which are incorporated by reference herein.

FIELD OF THE INVENTION

The invention relates to a process for modifying isocyanates, in which at least one organic isocyanate having an NCO functionality of >1 is oligomerized in the presence of at least one catalyst, and to the use of such a catalyst.

BACKGROUND OF THE INVENTION

The oligo- or polymerization of isocyanates, especially to form higher molecular weight oligomer mixtures having uretdione ("dimer"), isocyanurate ("trimer") and/or iminooxadiazinedione structures ("asymmetric trimer") in the molecular skeleton, has long been known. As can be seen above, the oligo- and polymerization of isocyanates are based in principle on the same chemical reactions. The reaction of a relatively small number of isocyanates with one another is referred to as oligomerization. The reaction of a relatively large number of isocyanates is referred to as polymerization. In the context of the present invention, the oligomerization or polymerization of isocyanates described above is referred to collectively as isocyanate modification or modification of isocyanates.

The modified polyisocyanates comprising free NCO groups, which optionally may also have been temporarily deactivated with blocking agents, are exceptionally high-quality starting materials for the preparation of a multiplicity of polyurethane plastics and coating compositions.

A series of industrial methods for isocyanate modification have been established in which the isocyanate to be modified, usually a diisocyanate, is generally reacted by addition of catalysts and these are then rendered inactive (deactivated) by suitable measures, when the desired degree of conversion of the isocyanate to be modified has been reached, and the polyisocyanate obtained is generally separated from the unreacted monomer. A summary of these methods from the prior art can be found in H. J. Laas et al., *J. Prakt. Chem.* 1994, 336, 185 ff.

Compounds with an ionic structure have proven to be effective as modification catalysts since they may be used in very low amounts, relative to the monomer to be reacted, and lead extremely rapidly to the desired result.

The option of also using tetraorganylammonium or -phosphonium as cation to the anion which is catalytically active toward isocyanates, such as hydroxide, alkanoate, alkoxylate, etc., is common knowledge, although generally not explicitly emphasized as being particularly preferred; cf.: H. J. Laas et al., *J. Prakt. Chem.* 1994, 336, 185 ff.

Additionally known is the use of fluorides and hydrogenpolyfluorides, the latter being stable adducts of HF onto compounds containing fluoride ions, optionally also in the form of their ammonium or phosphonium salts, for the isocyanate modification, from documents including EP 962 455 A1, EP 962 454 A1, EP 896 009 A1, EP 798 299 A1, EP 447 074 A1, EP 379 914 A1, EP 339 396 A1, EP 315 692 A1, EP 295 926 A1 and EP 235 388 A1.

However, the tetraorganylammonium and -phosphonium (hydrogenpoly)fluorides of the prior art, in the performance of the modification reaction, have the disadvantage that, when they are used, the reaction can sometimes be maintained only with continuous metered addition of catalyst, meaning that the breakdown of the catalyst in the isocyanate medium proceeds unacceptably quickly for technical purposes compared to the modification reaction.

An additional factor is that, when tetraorganylammonium (hydrogen)polyfluorides are used, an atypical reaction profile is sometimes observed, which leads to products having a much lower iminooxadiazinedione group content than in the case of a regular heat production rate profile (cf. EP 962 455 A1). According to the teaching of EP 962 455 A1, this disadvantage was eliminated by the use of phosphonium salts, but the latter—especially at relatively high reaction temperatures—have the unacceptably high tendency to decomposition mentioned further up, and the decomposition products can have an adverse effect on process and product stability.

EP 2 415 795 A1 claims, inter alia, very stable tetraorganylphosphonium (hydrogenpoly)fluorides that do not have these disadvantages, but they are not commercially available and are preparable only with difficulty.

SUMMARY OF THE INVENTION

The present invention provides an improved process for isocyanate modification, in which compounds that have good commercial availability or are easily preparable from inexpensive reactants are used as catalysts, these having a high catalytic activity and selectivity with simultaneously good catalyst stability.

These and other advantages and benefits of the present invention will be apparent from the Detailed Description of the Invention herein below.

DETAILED DESCRIPTION OF THE INVENTION

The present invention provides a process for modifying isocyanates, in which at least one organic isocyanate having an NCO functionality of >1 is oligomerized in the presence of at least one catalyst, characterized in that the catalyst comprises at least one cyclic ammonium salt having a cation of the formula I as catalysts for the isocyanate modification,

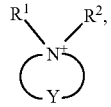

(Formula I)

wherein the N-substituents $R^1$ and $R^2$ are mutually independently identical or different aliphatic, cycloaliphatic, aromatic or araliphatic $C_1$-$C_{20}$ radicals, which are saturated or unsaturated, linear or branched, optionally substituted and/or interrupted by heteroatoms from the group of oxygen, sulfur and nitrogen and Y is a substituted or unsubstituted, linear or branched $C_2$-$C_{20}$ segment optionally interrupted by heteroatoms from the group of oxygen, sulfur, nitrogen and also by aromatic rings, and optionally comprising further rings.

Preferably, the references to "comprising", "containing", etc. mean "consisting essentially of" and most preferably "consisting of".

Compounds of the formula I are accessible in a simple manner by methods known from the literature (e.g. Houben-Weyl, *Methoden der Organischen Chemie,* 4th Ed., Vol. XI/2, pp. 591-640 and literature cited therein), for example by alkylating tertiary cyclic amines $R^1NY$ or $R^2NY$, where Y is a cyclic segment mentioned above, with haloalkanes $R^2$-Hal, or $R^1$-Hal and subsequent anion exchange, where halogen is Cl, Br and I, preferably Cl. Alternatively, in the case of carboxylates and also carbonates, it is also possible for example to alkylate directly with the carboxylic esters bearing $R^1$ or $R^2$ in the ester residue, methyl esters being preferred in this case.

Alternatively, the N-containing ring segment may also be obtained in the course of an (optionally simultaneously conducted) alkylation/quaternization reaction sequence of ammonia and also primary or secondary amines of the formulae $R^1NH_2$, $R^2NH_2$ or $R^1$, $R^2NH$.

In a first preferred embodiment, $R^1$ and $R^2$ in formula I are mutually independently identical or different $C_1$-$C_8$-alkyl substituents, preferably identical or different $C_1$-$C_6$-alkyl substituents and particularly preferably have a linear structure. These are accessible in a simple manner, for example, by reaction of optionally C-substituted pyrrolidines, piperidines and azepanes (1H-hexahydroazepines) with 1-haloalkanes such as for example chloromethane, bromomethane, iodomethane, chloroethane, bromoethane, iodoethane, 1-halopropanes, 1-halobutanes etc. and also the C-substituted derivatives thereof, where halogen is Cl, Br and I, preferably Cl.

In a further preferred embodiment, $R^1$ and $R^2$ in formula I are mutually independently identical or different benzyl radicals optionally substituted on the aromatic ring.

In addition, for example, by analogous reaction of compounds substituted on N by $R^1$ or $R^2$ (optionally C-substituted oxazolidines, isoxazolidines, oxazinanes, morpholines and oxazepanes and the analogs of the aforementioned N—O heterocycles which contain S rather than O, and also imidazolidines, pyrazolidines, piperazines and structurally related compounds) with the abovementioned haloalkanes, it is also possible to obtain compounds having a segment interrupted by heteroatoms in segment Y of the formula I.

Segment Y in formula I may also obviously have further rings. Examples include: 8-azabicyclo[3.2.1]octanes and also 2-azatricyclo[3.3.1.1$^{3,7}$]decanes (2-alkyl-2-azaadamantanes) substituted on the N-atom by $R^1$ or $R^2$ and derivatives thereof.

In the case of species containing two or more nitrogen atoms, it is additionally possible, by appropriate variation of the reaction conditions, also to produce salts having a doubly or multiply charged cation or, by prior suitable substitution of the nitrogen atom(s), to arrive at singly positively charged cations of the formula I in which one or more exocyclic alkyl substituent(s) is/are present on the trivalent nitrogen atom(s) of the Y ring.

Of course, it is also possible through suitable choice of the alkylating agent to introduce a structural variation into the ring segment Y; examples include reactions of bis(2-haloethyl) ethers with the abovementioned secondary amines $R^1$, $R^2NH$.

In a further preferred embodiment, segment Y is $C_4$-$C_6$-alkylene chains optionally substituted and/or interrupted by heteroatoms from the group of oxygen, sulfur, nitrogen and also by aromatic rings and especially has a linear structure.

Anions used in the compounds of the formula I may in principle be any species known to be catalytically active with respect to isocyanates, preference being given to hydroxide, alkanoate, carboxylate, heterocycles having at least one negatively charged nitrogen atom in the ring, especially azolate, imidazolate, triazolate, tetrazolate, fluoride, hydrogendifluoride, higher polyfluorides or mixtures of these, wherein the fluorides, hydrogendifluorides and higher polyfluorides (adducts of more than one equivalent HF onto compounds containing fluoride ions) lead in accordance with the invention to products having a high iminooxadiazinedione group content.

The catalysts of the invention can be used individually or in any desired mixtures with one another. For instance, solutions of quaternary ammonium hydroxides in various alcohols, depending on the pKa of the base and of the alcohol used, are present partially or completely as ammonium salts with alkoxide anion. This equilibrium can be shifted wholly to the side of complete alkoxide formation by removing the water of reaction resulting from this reaction. Suitable methods for water removal are all methods known from the literature for this purpose, especially azeotropic distillation optionally with the aid of a suitable entrainer.

By the modification process of the invention, a wide range of high-quality polyisocyanates, which are therefore very valuable for the polyurethane sector, is very generally obtainable in a simple manner. Depending on the starting (di)isocyanate used and the reaction conditions, the process of the invention affords polyisocyanates of what is known as the isocyanate trimer type (i.e. containing isocyanurate and/or iminooxadiazinedione structures) having a low proportion of uretdione groups ("isocyanate dimers"). In the case of rising reaction temperature, the proportion of the latter in the process products generally rises, but this effect is far less marked than when phosphonium salts with identical anion are used.

In the process of the invention, it may further be the case that the oligomerization is conducted in the presence of a solvent and/or additive.

For performance of the process of the invention, it is possible in principle to use any known mono-, di- or polyisocyanates from the prior art, individually or in any desired mixtures with one another.

Examples include: pentamethylene diisocyanate (PDI), hexamethylene diisocyanate (HDI), 2-methylpentane 1,5-diisocyanate, 2,4,4-trimethylhexane 1,6-diisocyanate, 2,2,4-trimethylhexane 1,6-diisocyanate, 4-isocyanatomethyloctane 1,8-diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)cyclohexane ($H_6XDI$), tolylene 2,4- and 2,6-diisocyanate (TDI), bis(4-isocyanatophenyl)methane (4,4'MDI), 4-isocyanatophenyl-2-isocyanatophenylmethane (2,4'MDI) and polycyclic products obtainable by formaldehyde-aniline polycondensation and subsequent conversion of the resulting (poly)amines to the corresponding (poly)isocyanates (polymer MDI).

Preference is given to aliphatic diisocyanates, i.e. diisocyanates in which both NCO groups are bonded to an sp3-hybridized carbon atom.

Particular preference is given to pentamethylene diisocyanate (PDI), hexamethylene diisocyanate (HDI), 2-methylpentane 1,5-diisocyanate, 2,4,4-trimethylhexane 1,6-diisocyanate, 2,2,4-trimethylhexane 1,6-diisocyanate, 4-isocyanatomethyloctane 1,8-diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI) and 1,3- and 1,4-bis(isocyanatomethyl)cyclohexane ($H_6XDI$).

It is irrelevant by which methods the aforementioned isocyanates are generated, i.e. with or without use of phosgene.

The amount of the catalyst to be used in the process according to the invention is guided primarily by the organic isocyanate used and the desired reaction rate and is preferably between ≥0.001 and ≤5 mol %, preferably between ≥0.002 and ≤2 mol %, based on the sum total of the molar amounts of the isocyanate used and of the catalyst.

In the process according to the invention, the catalyst may be used undiluted or dissolved in solvents. Useful solvents are all compounds which do not react with the catalyst and are capable of dissolving it to a sufficient degree, for example optionally halogenated aliphatic or aromatic hydrocarbons, alcohols, ketones, esters and ethers. Preference is given to using alcohols.

The process according to the invention can be conducted within the temperature range from 0° C. to +250° C., preferably 20° C. to 200° C., more preferably 40° C. to 150° C., and can be interrupted at any degrees of conversion, preferably after 5% to 80%, more preferably 10% to 60%, of the isocyanate used has been converted.

Catalyst deactivation can be accomplished in principle by employing a whole series of previously described prior art methods, for example the addition of (sub- or super-) stoichiometric amounts of acids or acid derivatives (e.g. benzoyl chloride, acidic esters of phosphorus- or sulfur-containing acids, these acids themselves, etc., but not HF), adsorptive binding of the catalyst and subsequent removal by filtration, and other methods known to those skilled in the art.

In a further preferred embodiment, unconverted organic isocyanate is removed after deactivation of the catalyst system by any method of the prior art, for example by (thin film) distillation or extraction, and subsequently preferably reused.

By contrast with catalysis by ammonium salts in which the charge-bearing nitrogen atom is not part of a ring system, when the catalysts according to the invention having fluoride or oligo-/polyfluoride anions are used, there is surprisingly no observation of any anomalies at all in the heat production rate, and a homogeneous reaction profile is always observed, which leads to high-quality products having an iminooxadiazinedione group content optimal for the particular reaction conditions.

It is quite generally the case that the catalysts according to the invention, irrespective of the anion which is responsible for the catalytic activity and selectivity, are much more stable in the organic isocyanate to be converted than the prior art derivatives known from the literature.

According to a particular continuously operating embodiment of the process according to the invention, the oligomerization can be undertaken continuously, for example in a tubular reactor.

The products or product mixtures obtainable by the process according to the invention are consequently versatile starting materials for production of optionally foamed plastic(s) and of paints, coating compositions, adhesives and additives. They are especially suitable for production of optionally water-dispersible one- and two-pack polyurethane paints, optionally in NCO-blocked form, because of their reduced solution and melt viscosity in comparison to (predominantly) isocyanurate polyisocyanate-based products with an otherwise equivalent or improved profile of properties. Thus, the HDI-based process products according to the invention, even in high dilution in paint solvents, are more stable to the occurrence of flocculation or turbidity than corresponding prior art products.

The process products according to the invention can be used pure or in conjunction with other prior art isocyanate derivatives, such as polyisocyanates containing uretdione, biuret, allophanate, isocyanurate and/or urethane groups, wherein the free NCO groups have optionally been deactivated with blocking agents.

The present invention further relates to the use of a cyclic ammonium salt having a cation of the formula I,

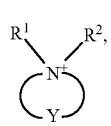

(Formula I)

wherein the N-substituents $R^1$ and $R^2$ are mutually independently identical or different aliphatic, cycloaliphatic, aromatic or araliphatic $C_1$-$C_{20}$ radicals, which are saturated or unsaturated, linear or branched, optionally substituted and/or interrupted by heteroatoms from the group of oxygen, sulfur and nitrogen and Y is a substituted or unsubstituted, linear or branched $C_2$-$C_{20}$ segment optionally interrupted by heteroatoms from the group of oxygen, sulfur, nitrogen and also by aromatic rings, and optionally comprising further rings, as catalysts for the oligomerization of organic isocyanates having an NCO functionality of >1.

The comparative examples and examples which follow are intended to further illustrate the invention but without limiting it.

EXAMPLES

All percentages, unless noted otherwise, are to be understood to mean percent by weight.

Mol % figures were determined by NMR spectroscopy and always relate, unless specified otherwise, to the sum total of the NCO conversion products. The measurements were effected on the BRUCKER DPX 400 or DRX 700 instruments on about 5% ($^1$H NMR) or about 50% ($^{13}$C NMR) samples in dry $C_6D_6$ at a frequency of 400 or 700 MHz ($^1$H NMR) or 100 or 176 MHz ($^{13}$C NMR). The reference employed for the ppm scale was small amounts of tetramethylsilane in the solvent with $^1$H NMR chemical shift 0 ppm. Alternatively, the $C_6D_5H$ present in the solvent was used as reference signal: $^1$H NMR chemical shift 7.15 ppm, $^{13}$C NMR chemical shift 128.02 ppm. Data for the chemical shift of the compounds in question were taken from the literature (cf. D. Wendisch, H. Reiff and D. Dieterich, *Die Angewandte Makromolekulare Chemie* 141, 1986, 173-183 and literature cited therein and also EP 896 009 A1).

The dynamic viscosities were determined at 23° C. using the viscometer HAAKE VT 550 in accordance with DIN EN ISO 3219. By measurements at different shear rates, it was ensured that the flow behavior of the polyisocyanate mixtures described according to the invention and also of the comparative products corresponds to that of ideal Newtonian fluids. The shear rate data can therefore be omitted.

The NCO content was determined by titration in accordance with DIN EN ISO 11909.

The residual monomer contents were determined by gas chromatography in accordance with DIN EN ISO 10283 using an internal standard.

All reactions were conducted under a nitrogen atmosphere unless stated otherwise.

The diisocyanates used are products of Covestro AG, D-51368 Leverkusen; all other commercially available chemicals were sourced from Aldrich, D-82018 Taufkirchen.

The catalysts not commercially available were obtained by methods known from the literature (cf. Houben-Weyl, *Methoden der Organischen Chemie,* 4th Ed., Vol. XI/2, pp. 591 ff and literature cited therein).

Examples 1 to 4 Catalyst Preparation

In each case, to 17.8 g (0.1 mol) of N-butyl-N-methylpyrrolidinium chloride, dissolved in ca. 65 g of 2-propanol (Example 1a) or ca. 180 g of 2-ethylhexanol (Examples 1b-1d), were added dropwise at room temperature:
- a) ca. 6.0 g of potassium hydroxide, as a saturated solution in methanol,
- b) ca. 12 g of potassium fluoride, as a saturated solution in methanol
- c) ca. 10 g of potassium acetate, as a saturated solution in methanol and respectively
- d) ca. 80 g of a ca. 20% potassium pivalate solution in methanol These mixtures were stirred for ca. 24 h and then filtered. The filter residue was washed three times with ca. 50 ml of 2-propanol, and each wash was followed by concentration under reduced pressure at room temperature, in order to substantially remove methanol (and in Examples 1b-1e also 2-propanol) and precipitate residues of inorganic salts. This was followed by another filtration and washing with about 10 ml of 2-propanol in each case and concentration as before. The respective combined filtrates were finally concentrated under reduced pressure to ca. 80 g (Example 1a) or ca. 150 g (Examples 1b-d) and analyzed.
- a) OH⁻ content* (by titration against 0.1 N HCl, phenolphthalein indicator): 2.0%*
- b) F⁻ content (ion sensitive electrode at pH=5.5): 1.1%.
- c) $CH_3C(O)O^-$ content (by titration against 0.1 N HCl, bromophenol blue indicator): 3.8%
- d) $(CH_3)_3CC(O)O^-$ content (by titration against 0.1 N HCl, bromophenol blue indicator): 6.4%.

Catalyst solution 1b was subsequently admixed with 1.8 g of anhydrous HF for conversion to the difluoride (catalyst solution 1e). * In the solutions of the hydroxides, NMR spectroscopy occasionally finds hints of the (partial) presence of the alkoxide corresponding to the solvent (2-propoxide or 2-ethyl hexanoate). For the sake of simplicity here, attention is always paid to the hydroxide ion, but the alkoxide anion—partially or exclusively—may also be present in solution.

Further catalysts 2-4 were obtained by an analogous process from the corresponding quaternary ammonium chloride, which for its part had optionally been prepared previously from the respective tertiary cyclic amine and the corresponding chloroalkane. Higher oligofluorides were obtained by adding appropriate excess HF to the fluoride solutions obtained in analogy to 1b).

Subsequently, the optimal catalyst concentration for the isocyanate trimerization was determined in exploratory preliminary experiments at 60° C. with HDI (cf. Example 5) and the concentration of the catalyst solution adjusted by dilution with 2-propanol or 2-ethylhexanol (in text below: 2-EH) such that only slight gel particle formation, if any, was observed when the catalyst solution was added to the HDI. An overview of this can be found in table 1. In the "solvent" column therein, only the alcohol added optionally for the further dilution of the starting solution is listed. If the catalysts obtained by the procedure described above for catalysts 1a to 1e were used without further dilution, the solvent is almost exclusively 2-EH with low residues of 2-propanol and optionally methanol (exception: Example 1a: exclusively 2-propanol and optionally methanol).

TABLE 1

Overview of the catalysts prepared (the catalyst concentration refers to the active compound (cation and anion))

| Example | Cation | Anion | Solvent | Concentration [%] |
|---|---|---|---|---|
| 1a | N-butyl-N-methylpyrrolidinium | OH⁻ | 2-PrOH | 20 |
| 1c | N-butyl-N-methylpyrrolidinium | $CH_3C(O)O^-$ | 2-EH | 2 |
| 1d | N-butyl-N-methylpyrrolidinium | $(CH_3)_3CC(O)O^-$ | 2-EH | 4 |
| 1e | N-butyl-N-methylpyrrolidinium | $[HF_2]^-$ | 2-EH | 8 |
| 2 | N,N-dimethylpyrrolidinium | OH⁻ | 2-PrOH | 20 |
| 3 | N-butyl-N-methylpiperidinium | $[HF_2]^-$ | 2-EH | 8 |
| 4 | N-methylmorpholinium | [F * 1.35 HF]⁻ | 2-PrOH | 15 |

Examples 5 to 11—Inventive Isocyanate Modifications

A jacketed flange vessel heated to the starting temperature desired in each case by means of an external circuit, having a stirrer, reflux condenser connected to an inert gas system (nitrogen/vacuum) and thermometer, was initially charged with 1000 g of HDI which was freed of dissolved gases by stirring under reduced pressure (<1 mbar) for one hour. After venting with nitrogen, the type and amount of catalyst specified in table 2 was metered in, optionally in portions, in such a way that the maximum temperature specified in table 2 was not exceeded. After ca. 1 mol of isocyanate groups had been converted, as indicated by attainment of an NCO content around 45.8%, the catalyst was deactivated by addition of an amount of the stopper specified in table 2 that was equivalent to the catalyst, and the mixture was stirred at reaction temperature for a further 30 min and subsequently worked up. The time between (first) catalyst addition and stopper addition is reported in table 2 as reaction time.

The workup was carried out by vacuum distillation in a thin-film evaporator of the flash evaporator (FE) type with a preevaporator (PE) connected upstream (distillation data:

pressure: 0.08+/−0.04 mbar, PE temperature: 120° C., ME temp.: 140° C.), with separation of unreacted monomer as distillate and the low-monomer polyisocyanate resin as bottom product (starting run). The polyisocyanate resin was separated and the distillate was collected in a second flange stirring apparatus of identical construction to the first, and made up to the starting amount (1000 g) with freshly degassed HDI. Thereafter, the mixture was treated again with catalyst and the procedure as described at the outset was followed. This procedure was repeated several times, optionally with variation of the reaction temperature (experiments A, B, C, etc.). The results can be found in table 2.

Finally, the distillate composition was ascertained by gas chromatography. In no case could decomposition products of the catalyst cation be detected (detection limit of ca. 20 ppm).

TABLE 2

Isocyanate modifications conducted

| Example | Catalyst (see Table 1) | Amount of catalyst [g] | Reaction temperature from-to [° C.] | Stopper* | Reaction time [min] |
|---|---|---|---|---|---|
| 5 A | 1a | 1.45 | 60 65 | 3 | 60 |
| 5 B | 1a | 1.16 | 60 83 | 3 | 4 |
| 5 C | 1a | 1.03 | 80 92 | 3 | 17 |
| 5 D | 1a | 0.89 | 80 85 | 3 | 20 |
| 5 E | 1a | 0.65 | 100 200 | 3 | 2[1)] |
| 5 F | 1a | 1.14[1)] | 100 125 | 3 | 24 |
| 6 A | 1c | 15.06 | 60 64 | 1 | 60 |
| 6 B | 1c | 12.15 | 60 63 | 1 | 90 |
| 6 C | 1c | 19.40 | 80 88 | 1 | 20 |
| 6 D | 1c | 16.67 | 80 83 | 1 | 30 |
| 6 E | 1c | 21.92 | 100 125 | 1 | 10 |
| 6 F | 1c | 21.56 | 100 104 | 1 | 15 |
| 7 A | 1d | 4.38 | 60 60 | 1 | 230 |
| 7 B | 1d | 4.26 | 60 64 | 1 | 120 |
| 7 C | 1d | 5.80 | 80 85 | 1 | 27 |
| 7 D | 1d | 5.95 | 80 84 | 1 | 25 |
| 7 E | 1d | 9.94 | 100 137 | 1 | 40 |
| 7 F | 1d | 9.55 | 100 101 | 1 | 70 |
| 8 A | 1e | 1.30 | 60 61 | 2 | 42 |
| 8 B | 1e | 0.94 | 60 62 | 2 | 30 |
| 8 C | 1e | 0.90 | 60 61 | 2 | 34 |
| 8 D | 1e | 1.00 | 60 61 | 2 | 28 |
| 8 E | 1e | 1.08 | 60 61 | 2 | 32 |
| 8 F | 1e | 0.83 | 60 61 | 2 | 45 |
| 9 A | 2 | 0.86 | 60 77 | 3 | 14 |
| 9 B | 2 | 0.90 | 60 62 | 3 | 25 |
| 9 C | 2 | 0.85 | 80 88 | 3 | 11 |
| 9 D | 2 | 0.60 | 80 92 | 3 | 7 |
| 9 E | 2 | 0.59 | 100 124 | 3 | 4 |
| 9 F | 2 | 0.79 | 100 103 | 3 | 8 |
| 10 A | 3 | 3.35 | 60 62 | 2 | 40 |
| 10 B | 3 | 3.46 | 60 61 | 2 | 30 |
| 10 C | 3 | 1.80 | 80 85 | 2 | 25 |
| 10 D | 3 | 1.87 | 80 83 | 2 | 15 |
| 10 E | 3 | 1.03 | 100 102 | 2 | 22 |
| 10 F | 3 | 1.16 | 100 105 | 2 | 19 |
| 11 A | 4 | 0.88 | 60 62 | 2 | 42 |
| 11 B | 4 | 0.84 | 60 61 | 2 | 50 |
| 11 C | 4 | 0.93 | 80 83 | 2 | 26 |
| 11 D | 4 | 0.90 | 80 82 | 2 | 18 |
| 11 E | 4 | 0.92 | 100 104 | 2 | 18 |
| 11 F | 4 | 0.84 | 100 104 | 2 | 18 |

*Stopper: 1: dibutyl phosphate, 2: toluenesulfonic acid, 40% in 2-PrOH, 3: dodecylbenzenesulfonic acid, 70% in 2-PrOH;
[1)]owing to the very high reactivity and short reaction time at the extreme exothermic peak in Example 5E, the catalyst 1a in Example 5F was previously diluted 1:1 with 2-propanol.

The resins obtained were, without exception, light-colored clear viscous liquids with no perceptible amine odor. In the case of use of the fluorine-containing catalysts, the result was mixtures of isocyanurate and iminooxadiazinedione along with a little uretdione. The proportion of iminooxadiazinedione groups is at a maximum at a reaction temperature around 60° C. and decreases when the reaction temperature is increased. In that case, there is increased formation of isocyanurate and uretdione, but the proportion of the latter increases much less significantly than in the case of catalysis with the corresponding quaternary phosphonium salts according to EP 962 455 A1. The oxygen-containing anions afford products of the isocyanurate type wherein the alcohol used as catalyst solvent is converted fully to the allophanate.

The invention claimed is:

1. A process for modifying isocyanates, in which at least one organic isocyanate having an NCO functionality of >1 is oligomerized in the presence of at least one catalyst, characterized in that the catalyst comprises at least one cyclic ammonium salt having a cation of the formula I as catalysts for the isocyanate modification,

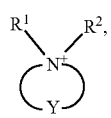

(Formula I)

wherein the N-substituents $R^1$ and $R^2$ are mutually independently identical or different aliphatic, cycloaliphatic, aromatic or araliphatic $C_1$-$C_{20}$ radicals, which are saturated or unsaturated, linear or branched, optionally substituted and/or interrupted by heteroatoms from the group of oxygen, sulfur and nitrogen and Y is a substituted or unsubstituted, linear or branched $C_2$-$C_{20}$ segment optionally interrupted by heteroatoms from the group of oxygen, sulfur, nitrogen and also by aromatic rings, and optionally comprising further rings.

2. The process as claimed in claim 1, characterized in that $R^1$ and $R^2$ are mutually independently identical or different $C_1$-$C_8$-alkyl substituents.

3. The process as claimed in claim 1, characterized in that $R^1$ and $R^2$ in formula I are mutually independently identical or different benzyl radicals optionally substituted on the aromatic ring.

4. The process as claimed in claim 1, characterized in that segment Y is $C_4$-$C_6$-alkylene chains optionally substituted and/or interrupted by heteroatoms from the group of oxygen, sulfur, nitrogen and also by aromatic rings and especially has a linear structure.

5. The process as claimed in claim 1, characterized in that the anion of the cyclic ammonium salt is selected from hydroxide, alkanoate, carboxylate, heterocycles having at least one negatively charged nitrogen atom in the ring, especially azolate, imidazolate, triazolate, tetrazolate, fluoride, hydrogendifluoride, higher polyfluorides or mixtures of these.

6. The process as claimed in claim 1, characterized in that the oligomerization is conducted in the presence of a solvent and/or additive.

7. The process as claimed in claim 1, characterized in that the organic isocyanate is selected from the group consisting of pentamethylene diisocyanate, hexamethylene diisocyanate, 2-methylpentane 1,5-diisocyanate, 2,4,4-trimethylhexane 1,6-diisocyanate, 2,2,4-trimethylhexane 1,6-diisocyanate, 4-isocyanatomethyloctane 1,8-diisocyanate, 3(4)-isocyanatomethyl-1-methylcyclohexyl isocyanate, isophorone diisocyanate, 1,3- and 1,4-bis(isocyanatomethyl) benzene, 1,3- and 1,4-bis(isocyanatomethyl)cyclohexane or mixtures of these.

8. The process as claimed in claim 1, characterized in that the catalyst of the formula I is used in an amount between >0.001 and <5 mol %, based on the sum total of the molar amounts of the isocyanate used and of the catalyst.

9. The process as claimed in claim 1, characterized in that the process is conducted within the temperature range from 0° C. to +250° C.

10. The process as claimed in claim 1, characterized in that the oligomerization is stopped after 5% to 80% by weight of the organic isocyanate used has been converted.

11. The process as claimed in claim 10, characterized in that the oligomerization is stopped by deactivating the catalyst, especially by addition of an acid or an acid derivative such as benzoyl chloride, an acidic ester of phosphorus- or sulfur-containing acids, these acids themselves, adsorptive binding of the catalyst and subsequent removal by filtration or combinations thereof.

12. The process as claimed in claim 10, characterized in that unconverted organic isocyanate is removed from the reaction mixture.

13. The process as claimed in claim 1, characterized in that $R^1$ and $R^2$ are mutually independently identical or different $C_1$-$C_6$-alkyl substituents.

14. The process as claimed in claim 1, characterized in that $R^1$ and $R^2$ are mutually independently identical or different $C_1$-$C_8$-alkyl substituents and have a linear structure.

15. The process as claimed in claim 1, characterized in that the catalyst of the formula I is used in an amount between >0.002 and <2 mol %, based on the sum total of the molar amounts of the isocyanate used and of the catalyst.

16. The process as claimed in claim 1, characterized in that the process is conducted within the temperature range from 20 to 200° C.

17. The process as claimed in claim 1, characterized in that the process is conducted within the temperature range from 40 to 150° C.

18. The process as claimed in claim 1, characterized in that the oligomerization is stopped after 10% to 60% by weight of the organic isocyanate used has been converted.

* * * * *